US008834613B2

(12) United States Patent
Kwon et al.

(10) Patent No.: US 8,834,613 B2
(45) Date of Patent: Sep. 16, 2014

(54) BAD ODOR REMOVAL SYSTEM FOR SEWAGE PIPE

(75) Inventors: Yong Sog Kwon, Uiwang-si (KR); Sung Chang Hong, Seoul (KR); Shi Cheol Shin, Gunpo-si (KR); Sun Tae Kim, Yongin-si (KR)

(73) Assignee: Scentec Inc., Gunpo-si, Gyeonggi-do (KR)

( * ) Notice: Subject to any disclaimer, the term of this patent is extended or adjusted under 35 U.S.C. 154(b) by 0 days.

(21) Appl. No.: 13/878,285

(22) PCT Filed: Oct. 7, 2011

(86) PCT No.: PCT/KR2011/007448
§ 371 (c)(1),
(2), (4) Date: May 9, 2013

(87) PCT Pub. No.: WO2012/047062
PCT Pub. Date: Apr. 12, 2012

(65) Prior Publication Data
US 2013/0312613 A1    Nov. 28, 2013

(30) Foreign Application Priority Data

Oct. 7, 2010 (KR) .................. 10-2010-0097885
Dec. 28, 2010 (KR) .................. 10-2010-0136954
Dec. 28, 2010 (KR) .................. 10-2010-0136955

(51) Int. Cl.
B01D 53/02      (2006.01)
E03F 5/08       (2006.01)
A61L 9/00       (2006.01)
F24F 3/16       (2006.01)

(52) U.S. Cl.
CPC ... *A61L 9/00* (2013.01); *E03F 5/08* (2013.01); *F24F 2003/1689* (2013.01)
USPC .................. 96/108; 95/141; 95/257

(58) Field of Classification Search
USPC ...................... 96/108; 95/141, 257
See application file for complete search history.

(56) References Cited

U.S. PATENT DOCUMENTS 4,094,773 A * 6/1978 Beaumont ............ 210/612
4,454,427 A * 6/1984 Sosnowski et al. ...... 290/2
(Continued)

FOREIGN PATENT DOCUMENTS

JP       07-054392 A     2/1995
KR       10-0738438 B1   7/2007
(Continued)

*Primary Examiner* — Christopher P Jones
(74) *Attorney, Agent, or Firm* — Sherr & Jiang, PLLC (57) ABSTRACT

The present invention relates to a bad odor removal system that is applied to a long sewage pipe, and provides a bad odor removal system for a swage pipe, and the system basically comprises: deodorizers which are installed at certain intervals on the upper part of the sewage pipe; and a bad odor ventilating device which is installed on the inside of the sewage pipe in connection with said deodorizers, and includes a cooling device, wherein an air flow blocking membrane is installed on the inside of the sewage pipe and bad odor dispersion-preventive plates that actively operate are installed on an outlet and a manhole, thereby effectively blocking all kinds of bad odors that may be generated from the entire sewage pipe.

14 Claims, 8 Drawing Sheets

(56) References Cited

U.S. PATENT DOCUMENTS

| | | | |
|---|---|---|---|
| 5,257,466 A * | 11/1993 | Kishi | 34/95 |
| 6,528,021 B1 * | 3/2003 | Williams | 422/121 |
| 7,240,865 B2 * | 7/2007 | Choi | 241/46.014 |
| 7,845,586 B2 * | 12/2010 | Lee | 241/65 |
| 8,337,759 B1 * | 12/2012 | Alford et al. | 422/123 |
| 2009/0307831 A1 * | 12/2009 | Shahar | 4/216 |

FOREIGN PATENT DOCUMENTS

| | | |
|---|---|---|
| KR | 10-2009-0026520 A | 3/2009 |
| KR | 10-2009-0061363 A | 6/2009 |
| KR | 10-0949164 B1 | 3/2010 |
| KR | 10-0982338 B1 | 9/2010 |

* cited by examiner

BAD ODOR REMOVAL SYSTEM FOR SEWAGE PIPE

CROSS REFERENCE TO PRIOR APPLICATIONS

This application is a National Stage Patent Application of PCT International Patent Application No. PCT/KR2011/007448 (filed on Oct. 7, 2011) under 35 U.S.C. §371, which claims priority to Korean Patent Application Nos. 10-2010-0097885 (filed on Oct. 7, 2010), 10-2010-0136954 (filed on Dec. 28, 2010) and 10-2010-0136955 (filed on Dec. 28, 2010), which are all hereby incorporated by reference in their entirety.

TECHNICAL FIELD

The present invention relates to a bad odor removal system for a sewage pipe, and more particularly, to a bad odor removal system for a sewage pipe, the system capable of maintaining negative pressure in the sewage pipe by sucking out a bad odor accumulated in the sewage pipe with high density to reduce the density and ejecting the same and capable of effectively preventing dispersion of the bad odor by using a shielding device installed at a sewerage manhole or a sewage outlet.

BACKGROUND ART

Generally, domestic sewage discharged from residential facilities and rainwater flowing via rainwater pipes pass through sewage pipes, are collected at a septic tank, and then transferred to a sewage treatment plant. However, in our country (in Korea), a combined sewage system is employed in which the domestic sewage and the rainwater are mixed and discharged together, which causes various problems.

In detail, in the case of the combined sewage system, since a flow velocity is slow due to a low incline needed for allowing sewage to flow, pollutants are easily deposited in such a way that residual pollutants are decomposed, thereby causing a bad odor.

However, since the rainwater pipe for allowing rainwater to flow is installed at the combined sewage system to have an open structure, as described above, the bad odor generated inside a sewage pipe may be dispersed toward residential areas or roads.

Accordingly, rainwater pipes near residential facilities, stores, and restaurants may be blocked using rubber plates to prevent the bad odor, effects of which fail to satisfy expectation. Particularly, when it rains, to prevent an overflow of sewage or rainwater, it is necessary to remove the rubber plates in such a way that the bad odor still remains.

Also, it may be considered to set a carrier adsorbing and removing bad-smelling materials afloat inside the sewage pipe. In this case, when amounts of sewage and rainwater increase, the carrier may be often swept away and it is hard to expect an effect of removing a bad odor.

On the other hand, recently, there is provided a method of installing fans with certain intervals to extract a bad odor in one direction. However, as described above, since a sewage pipe has an open structure connected to a rainwater pipe and a plurality of branch pipes and a length thereof is very great, it is very difficult to form negative pressure thereinside. Accordingly, in this condition, it is almost impossible to prevent dispersion of a bad odor by operating fans.

Also, a bad odor with high density, which is deposited for a long time and hardly ever floats, exists inside the sewage pipe. Since bad odor removal systems, which have been developed, are almost installed at upper parts of sewage pipes, certain limitations exist in removing the bad odor with high density.

DISCLOSURE OF THE INVENTION

Technical Problem

An aspect of the present invention provides a bad odor removal system for a sewage pipe, capable of preventing atmospheric diffusion of a bad odor by continuously maintaining negative pressure inside the long sewage pipe.

An aspect of the present invention also provides a bad odor removal system for a sewage pipe, capable of removing not only a bad odor with low density existing in an upper part of the sewage pipe but a bad odor with high density existing in a lower part thereof at a single stroke.

An aspect of the present invention also provides a bad odor removal system for a sewage pipe, capable of a bad odor that may occur at a sewerage manhole and a sewage outlet, that is, ends of the sewage pipe at a single stroke.

An aspect of the present invention also provides a bad odor removal system for a sewage pipe, capable of effectively responding to a case in which the amount of sewage or rainwater rapidly increases.

Technical Solution

According to an aspect of the present invention, there is provided a bad odor removal system for a sewage pipe, the system including deodorizers installed at an upper part of the sewage pipe with certain intervals and a bad odor ventilating device connected to the deodorizers and installed inside the sewage pipe, in which each of the deodorizers includes a cooling device.

In this case, the bad odor ventilating device may include a sucking unit connected to each of the deodorizers installed on an inner top end of the sewage pipe, an exhausting unit installed in the sucking unit, and a blast fan installed between the exhausting unit and the deodorizer.

In this case, the sucking unit may include a support frame vertically installed on the inner top end of the sewage pipe, a sucking chamber installed inside the support frame and folded to be multistage, a fan belt connecting the sucking chamber, and a driving motor coupled with the fan belt.

Also, the exhausting unit may include an exhausting chamber coupled with the fan belt to be foldable to be multistage inside the sucking chamber.

On the other hand, at least one damper capable of being open and closed may be installed outside one of the sucking chamber and the exhausting chamber.

In this case, the system may further include a controller adjusting a direction of an air flow inside the sewage pipe by controlling operations of the respective components.

In the present embodiment, a plurality of air flow blocking membranes is installed inside the sewage pipe to form a space for each of the deodorizers.

In this case, each of the plurality of air blocking membranes may include supporters installed on the inner top end of the sewage pipe, a blocking membrane coupled with the supporters and divided with certain intervals, at least one wrinkle-preventive bar installed on the blocking membrane in a width direction, and centroid weights inserted into water-soluble or insoluble bags installed at a bottom of the blocking membrane.

In this case, the system may further include a hinge installed at a sewerage manhole diverged from the sewage pipe and connected to the ground, a bad odor dispersion-preventive plate coupled with the hinge, and a spring installed to the hinge and elastically pushing up the bad odor dispersion-preventive plate.

Also, the system may further include a bad odor dispersion-preventive pipe installed at an end of the sewage pipe, a division strip installed inside the bad odor dispersion-preventive pipe and dividing the bad odor dispersion-preventive pipe into an upper space and a lower space, and bad odor dispersion-preventive plates installed outward at ends of the upper space and the lower space to be pivotable.

In this case, a bad odor inlet port connected to a separate one of the deodorizers may be formed on an upper part of the bad odor dispersion-preventive pipe.

Also, an air curtain device may be installed at the end of the sewage pipe.

In this case, the air curtain device may include a guide rail vertically installed at the end of the sewage pipe, an air curtain bar coupled with the guide rail to be slidable and connected to the deodorizer, and a motor driving the air curtain bar.

In this case, a sensor may be installed on the air curtain bar.

Advantageous Effects

It is possible to prevent dispersion of a bad odor by inducing negative pressure by dividing the inside of a sewage pipe by using air flow blocking membranes.

Also, a bad odor ventilating device installed inside the sewage pipe is formed to be foldable to be withdrawn as multiple stages, thereby removing a bad odor with high density deposited in a lower part of the sewage pipe.

In addition, bad odor dispersion-preventive plates actively controlled are installed at a sewerage manhole and a sewage outlet diverged from the sewage pipe, respectively, thereby curbing a bad odor capable of being dispersed outward as much as possible.

Additionally, a flexible and highly durable air flow blocking plate is installed inside the sewage pipe, thereby effectively preventing dispersion of a bad odor although the amount of rainwater rapidly increases.

MODE FOR CARRYING OUT THE INVENTION

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Also, in the drawings, for clear description, a part having no connection with the description will be omitted and like reference numerals designate like elements throughout.

Embodiment 1

A bad odor removal system for a sewage pipe according to an embodiment of the present invention basically prevents external dispersion of a bad odor by forming negative pressure inside the sewage pipe, and additionally, removes a bad odor with high density deposited in a lower part of the sewage pipe for a long time together with bad odors dispersed via a sewerage manhole and a sewage outlet at a single stroke, thereby totally controlling all kinds of bad odors, which will be sequentially described below.

Figure 1:
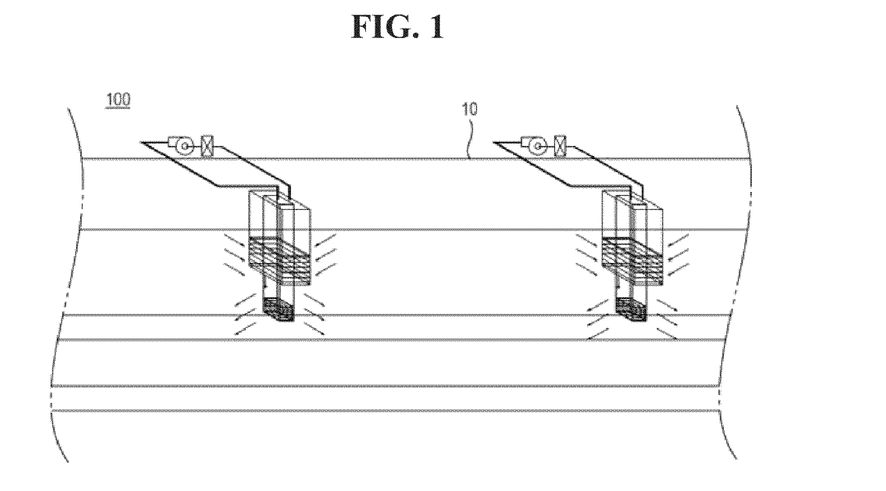
FIG. 1 is a view illustrating a bad odor removal system for a sewage pipe according to a first embodiment of the present invention.
Figure 2:
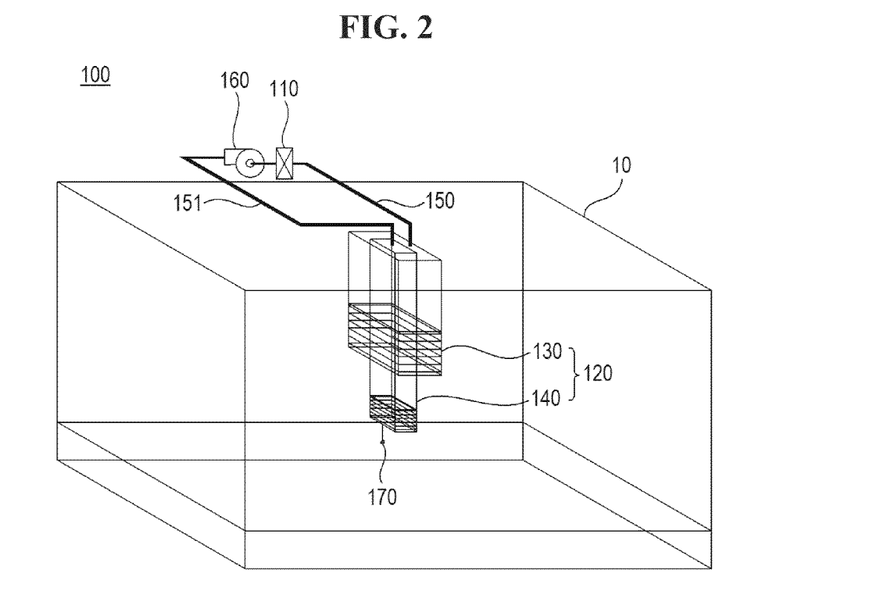
FIG. 2 is an enlarged view illustrating an intermediate part of the bad odor removal system according to the first embodiment.

FIG. 1 is a view illustrating a bad odor removal system 100 for a sewage pipe according to a first embodiment of the present invention, and FIG. 2 is an enlarged view illustrating an intermediate part of the bad odor removal system 100.

As shown in FIGS. 1 and 2, the bad odor removal system 100 includes deodorizers 110 and a bad odor ventilating device 120.

The deodorizers 110 are elements to deodorize, sterilize, cool down, and exhaust a bad odor sucked via the bad odor ventilating device 120 and is installed in an upper part of the sewage pipe 10 with uniform intervals and is connected to the bad odor ventilating device 120 via a sucking duct 150 and an exhausting duct 151. In the present embodiment, the deodorizer 110 is not particularly limited and may be any one capable of deodorizing, sterilizing, cooling down, and exhausting, which are described above.

The bad odor ventilating device 120 is a component to suck a bad odor existing in the sewage pipe 10 to be processed by the deodorizer 110 and eject the same toward the sewage pipe 10, which is installed inside the sewage pipe 10 with certain intervals.

In detail, the bad odor ventilating device 120 includes a sucking unit 130 installed on an inner top end of the sewage pipe 10, an exhausting unit 140 installed inside the sucking unit 130, and a blast fan 160 installed between the deodorizer 110 and the exhausting unit 140, thereby sucking and exhausting the bad odor. For this, the sucking unit 130 and the exhausting unit 140 are connected to the deodorizer 110 via the sucking duct 150 and the exhausting duct 151, respectively.

Hereinafter, the bad odor ventilating device 120 will be described below in detail with reference to other drawings.

Figure 3:
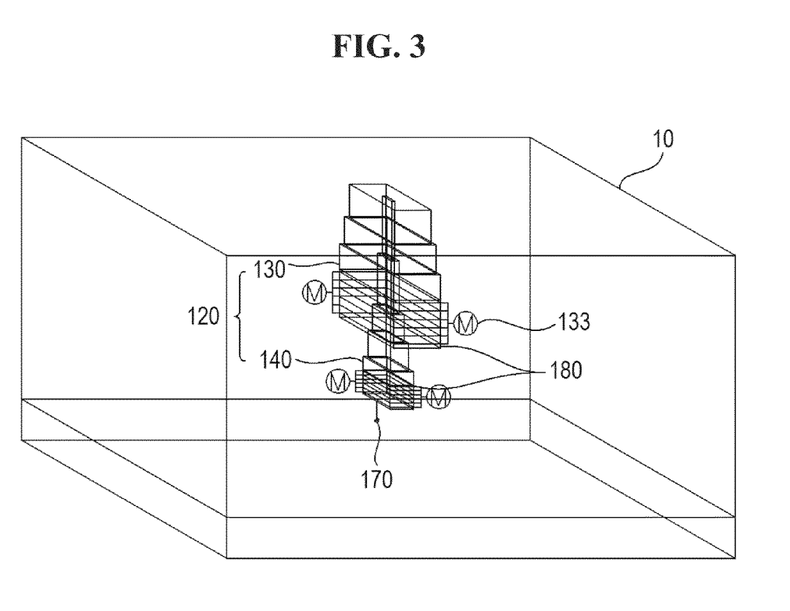
FIG. 3 is a bad odor ventilating device of the bad odor removal system according to the first embodiment.
Figure 4:
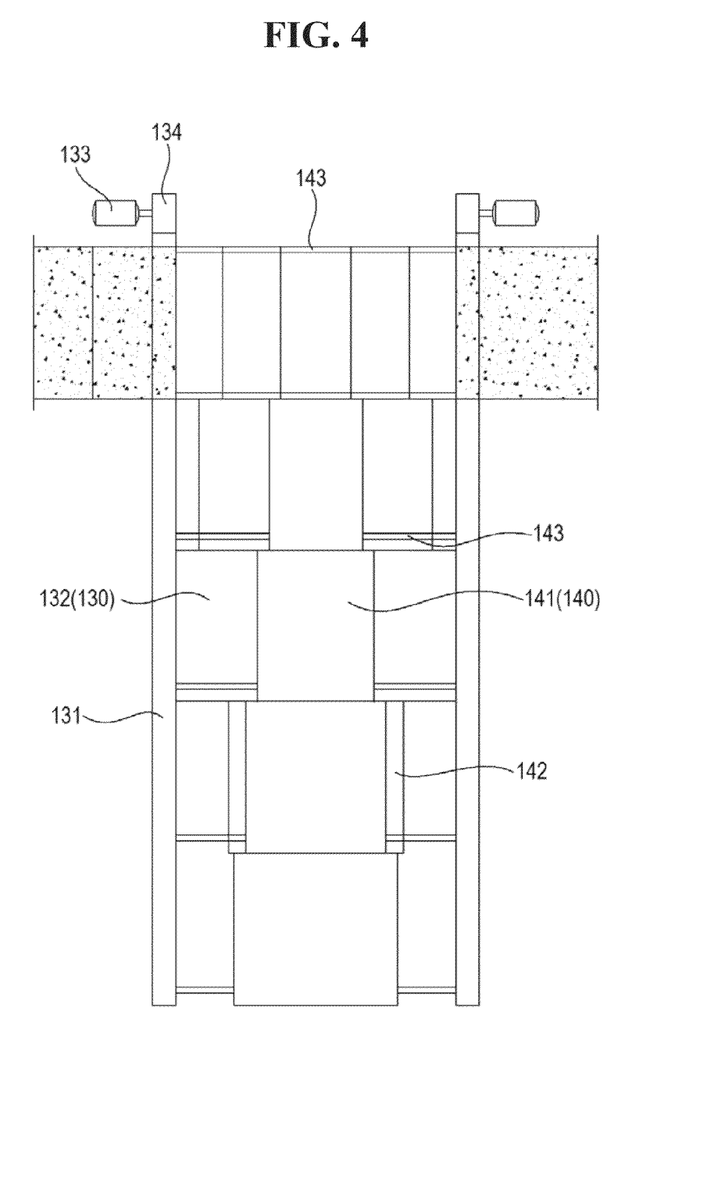
FIG. 4 is a cross-sectional view illustrating the bad odor ventilating device of the bad odor removal system according to the first embodiment.
Figure 5:
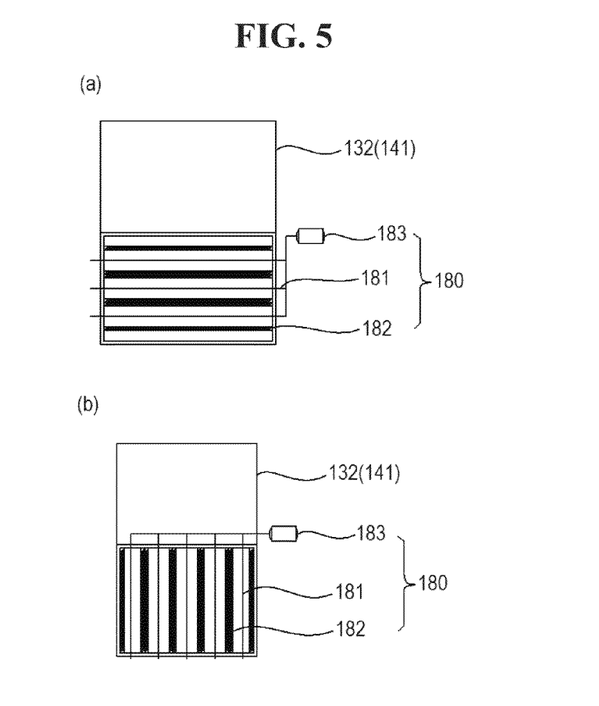
FIG. 5 is a view illustrating a damper of the bad odor ventilating device of the bad odor removal system according to the first embodiment.

FIG. 3 is the bad odor ventilating device 120 of the bad odor removal system 100, FIG. 4 is a cross-sectional view illustrating the bad odor ventilating device 120, and FIG. 5 is a view illustrating a damper of the bad odor ventilating device 120.

Referring to FIGS. 3 to 5, the sucking unit 130 and the exhausting unit 140 are formed to be foldable to vertically move in the bad odor ventilating device 120.

In detail, the sucking unit 130 includes a support frame 131 vertically installed on the inner top end of the sewage pipe 10, a sucking chamber 132 installed inside the support frame 131 and folded to be multistage, a fan belt (not shown) connecting the sucking chamber 132, and a driving motor 133 coupled with the fan belt by using a pulley 134. The exhausting unit 140 includes an exhausting chamber 141 installed inside the sucking chamber 132 to be foldable to be multistage. In this case, identical to the sucking chamber 132, the exhausting chamber 141 is coupled with the fan belt and vertically moves using the driving motor 133. Also, multistage-withdrawn structures of the sucking chamber 132 and the exhausting chamber 141 may be formed similar to a structure of a general antenna used for a radio or a vehicle or formed by a method of connecting and assembling respective chambers by using a plurality link members, LM guides, and gears but not limited thereto.

On the other hand, the sucking chamber 132 and the exhausting chamber 141 are divided by a partition 142 to ascend and descend with certain intervals and simultaneously with being supported by a plurality of supports 143 to provide a strong supporting force. In the present embodiment, shapes of the sucking chamber 132 and the exhausting chamber 141 may be various such as a rectangular parallelepiped or a regular hexahedron if necessary and but not limited thereto. In this case, at a bottom of the exhausting chamber 141, a sensor 170 for sensing an air pollution degree, a temperature, humidity, air flow, water level, and the like inside the sewage pipe 10 may be installed.

When configuring the sucking unit 130 and the exhausting unit 140 to be withdrawn downwardly as described above, it is possible to remove not only a bad odor with low density existing in the upper part of the sewage pipe 10 but a bad odor with high density deposited in the lower part thereof.

In detail, as described above, the deodorizer 110 not only sterilizes and removes a bad odor but cools down the same. In the present embodiment, a cooling unit (not shown) for cooling down is installed together with the sucking unit 130 and the exhausting unit 140, thereby removing the bad odor with high density simultaneously with inducing negative pressure inside the sewage pipe 10.

That is, when withdrawing and operating the sucking unit 130 and the exhausting unit 140 downwardly as much as possible, a bad-smelling gas with high density existing at the lower part of the sewage pipe 10 is sucked and the sucked bad-smelling gas is cooled down by the cooling unit in such way that steam included in the gas is frozen and drops down to the bottom of the sewage pipe 10. As a result thereof, the bad-smelling gas initially sucked is ejected toward the bottom of the sewage pipe 10 via the exhausting chamber 141 while being reduced in mass as much as an amount of the frozen steam, thereby causing movement of a negative-consolidated air flow due to a difference in density to reduce dispersion of a bad odor.

On the other hand, outside the sucking unit 130 and the exhausting unit 140, a plurality of dampers 180 may be installed. The dampers 180 are components to control an air flow inside the sewage pipe 10 by controlling suction and exhaust angles, which are installed at a lowest one of the sucking unit 132 and the exhausting unit 141 or a plurality of chambers in a proper number thereof.

In detail, each of the dampers 180 includes damper axes vertically or horizontally installed inside the respective chambers 132 and 141, damper members 182 coupled with the damper axes 181, and a driving motor 183 controlling rotations of the damper axes 181. Accordingly, when operating the driving motor 183, the damper axes 181 rotate, thereby opening and closing the damper members 182. In the present embodiment, opening and closing the damper members 182 may be performed separately or simultaneously.

In this case, since the dampers 180 are installed at front, rear, left, and right sides in the sucking chamber 132 and installed at a lower part in addition to front, rear, left, and right sides in the exhausting chamber 141, it is possible to control an air flow in all directions. However, the location, structure, and number of the dampers 180 are not limited thereto and may be variously changed if possible to control the air flow inside the sewage pipe 10 in a certain direction.

In the present embodiment, vertical movements of the sucking unit 130 and the exhausting unit 140, opening and closing and suction and exhaust angles of the damper members 180, and turning on/off the deodorizer 110 are performed by a control device (not shown). That is, the control device receives information gathered from the sensor 170 and controls operations of the respective components, thereby regularly controlling the direction of the air flow.

As described above, the bad odor removal system 100 for the sewage pipe 10 has been described. Hereinafter, another embodiment of the present invention will be described below with reference to the drawings.

Embodiment 2

A bad odor removal system 200 according to a second embodiment of the present invention, similar to the bad odor removal system 100, prevents dispersion of a bad odor by forming negative pressure inside the sewage pipe 10 and simultaneously with removing bad odors of a sewerage manhole and a sewage outlet connected to the outside, which will be described sequentially below with reference to the drawings.

Figure 6:
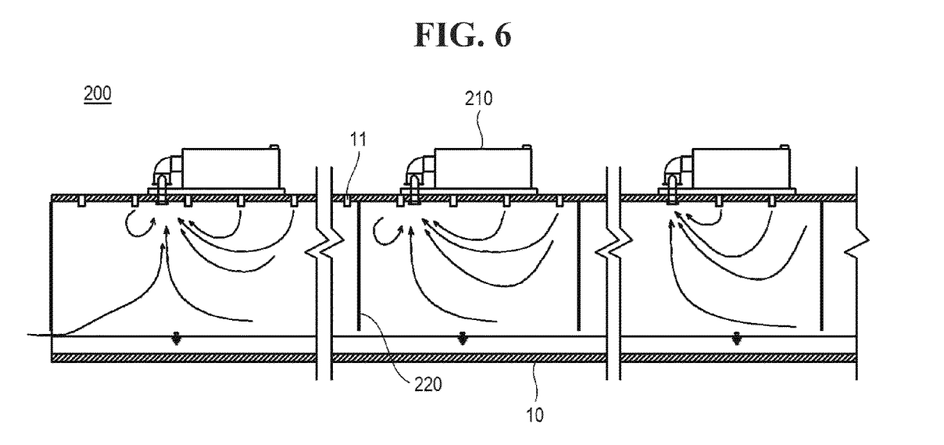
FIG. 6 is a view illustrating a bad odor removal system for a sewage pipe according to a second embodiment of the present invention.
Figure 7:
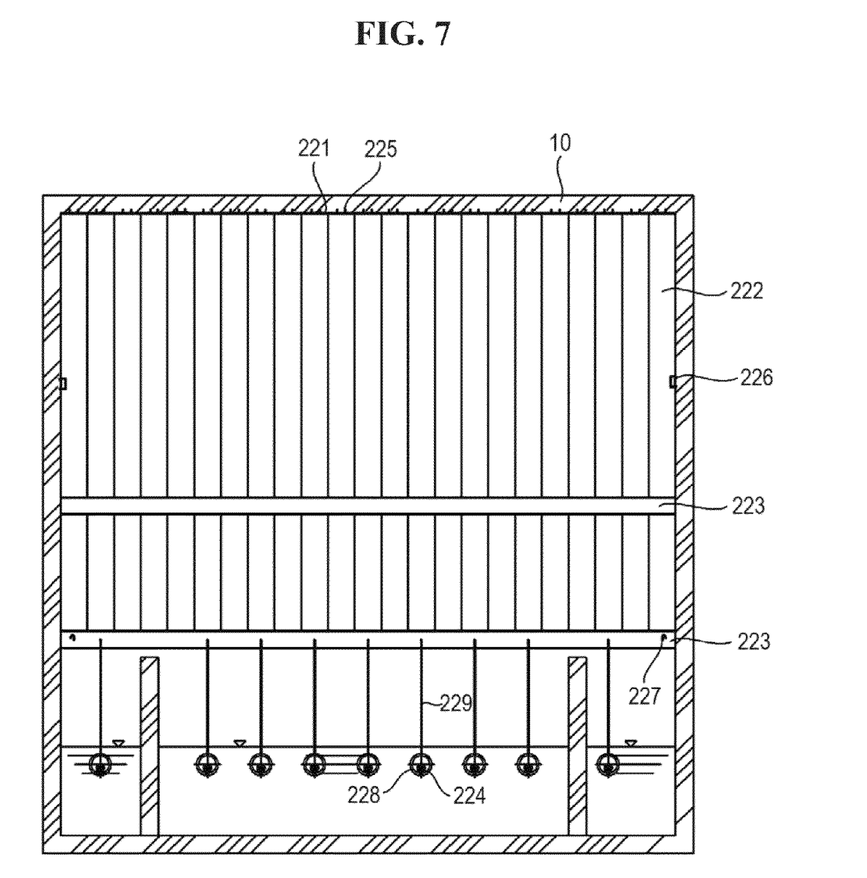
FIG. 7 is a view illustrating air flow blocking membranes of the bad odor removal system according to the second embodiment of the present invention.

FIG. 6 is a view illustrating the bad odor removal system 200 for the sewage pipe 10 according to the second embodiment of the present invention, and FIG. 7 is a view illustrating air flow blocking membranes of the bad odor removal system 200.

As shown in FIGS. 6 and 7, the bad odor removal system 200 may include air flow blocking membranes 220 inside the sewage pipe 10. Referentially, in the drawings, a reference numeral 210 designates a deodorizer whose configuration and functions are identical to Embodiment 1.

The air flow blocking membranes 220 are to effectively block a bad odor when an amount of sewage is rapidly changed and are installed with certain intervals to form a space for each of the deodorizers 210. Each of the air flow blocking membranes 220 includes supporters 221, a blocking membrane 222, wrinkle-preventive bars 223, and centroid weights 224.

In detail, the supporters 221 are installed in an internal upper end of the sewage pipe 10 in a longitudinal direction with certain intervals. In this case, an installation interval of the supporters 221 may be accurately controlled by considering a length and a size of the sewage pipe 10 and the number and a capacity of the deodorizers 210. Referentially, a reference numeral 11, which is shown in FIG. 6 but not described, designates a rainwater pipe.

The blocking membrane 222 is installed at the supporter 221, respectively and divides a space inside the sewage pipe 10, thereby blocking dispersion of the bad odor. As the blocking membrane 222, a flexible material such as vinyl, resin, and a tent may be used to be smoothly drawn not to be damaged by a flow of rainwater rapidly increasing due to heavy rain and the like.

In this case, when installing the blocking membrane 222, hinges 225 may be used. That is, the hinge 225 is installed at the supporter 221 to be pivotable in a direction in which sewage flows and a top end of the blocking membrane 222 is coupled with the hinge 225 in such a way that the blocking membrane 222 is more smoothly drawn although the sewage or rainwater suddenly increases, thereby not only preventing dispersion of the bad odor regardless of a flow of the sewage but improving durability with no damage neither tear.

On the other hand, to reduce an effect caused by increase of the sewage, the blocking membrane 222 may be divided. That is, when cutting and dividing the blocking membrane 222 with certain intervals in a width direction, the sewage may easily pass through when including a material of great volume. Also, although a part of the blocking membrane 222 is damaged, since a certain air flow may be blocked, it is still possible to prevent the dispersion of the bad odor.

As described above, when forming the blocking membrane 222 to be divided, a wrinkle-preventive bar 223 may be additionally included. When being divided, since the blocking membrane 222 may be twisted by the air flow or the sewage in such a way that blocking the air flow is impossible, it is necessary to maintain the blocking membrane 222 in a certain form. In this case, the wrinkle-preventive bars 223 may be installed in an intermediate part and a lower part of the blocking membrane 222, respectively, but may be controlled to be an appropriate number thereof if necessary.

Also, the blocking membrane 222 is generally installed to be separate from the sewage with a certain height, which may be controlled according to water level of the sewage or the rainwater. That is, when it rains heavily like in summer, since the rainwater increases, the blocking membrane 222 may be torn by water pressure, thereby dispersing the bad odor. Accordingly, in the present embodiment, to prevent this, latches 226 are installed at an inner wall of the sewage pipe and hooks 227 are formed on both sides of the wrinkle-preventive bar 223 in such a way that the hooks are hung on the latches 225, respectively, thereby controlling the height.

When being formed as described above, since the blocking membrane 222 may be taken down in winter and may be lifted by coupling the hooks 227 with the latches 226 in summer, it is possible to rapidly convert a state thereof depending on an amount of rainfall.

At least one centroid weight 224 is installed at a bottom of the blocking membrane 222 to allow the blocking membrane 222 to be maintained as being always unfolded, thereby providing airtightness.

In this case, when being installed, the centroid weight 224 may be directly coupled with the blocking membrane 222. However, as described above, since the blocking membrane 222 may be easily torn due to the flexible material thereof, the centroid weight 224 may be coupled with the wrinkle-preventive bar 223. On the other hand, the number and weight of the installed centroid weights 224 may vary with the size of the sewage pipe 10 and the amount of the sewage.

Additionally, the centroid weight 224 may be installed while being inserted into a bag 228 formed of a water-soluble material. That is, when inserting the centroid weight 224 into the bag 228 and connecting the same to the blocking membrane 222 by using a string 229 for connection in such a way that the bag 228 is solved in rainwater and the centroid weight 224 is naturally separated when the amount of rainfall increases. As described above, when the centroid weight 224 is separated, since the blocking membrane 222 is drawn back according to a flow of the rainwater, it is possible to prevent being damaged from the pressure of suddenly increased rainwater. In this case, the material for the bag 228 is not particularly limited and may be any well-known soluble material.

As described above, the air flow blocking membrane installed inside the sewage pipe 10 in the bad odor removal system 200 has been described. However, the bad odor removal system 200 for the sewage pipe 10 may remove not only a bad odor inside the sewage pipe 10 but a bad odor generated in a sewerage manhole, which will be described below in detail with reference to the drawings.

Figure 8:
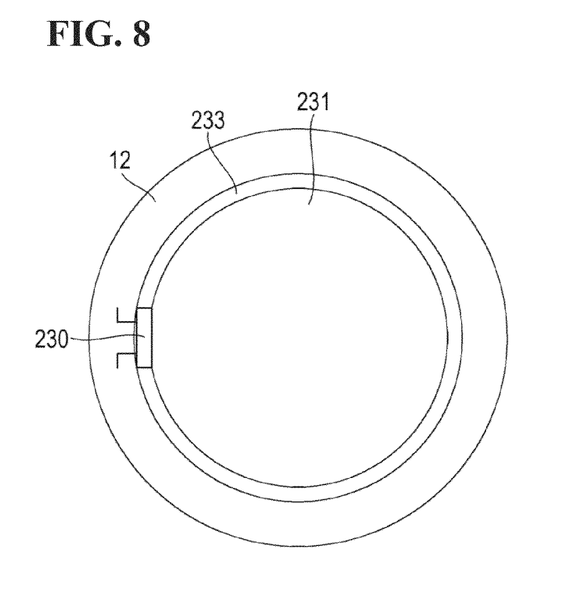
FIG. 8 is a horizontal cross-sectional view illustrating a configuration of the bad odor removal system, installed in a sewerage manhole, according to the second embodiment of the present invention.
Figure 9:
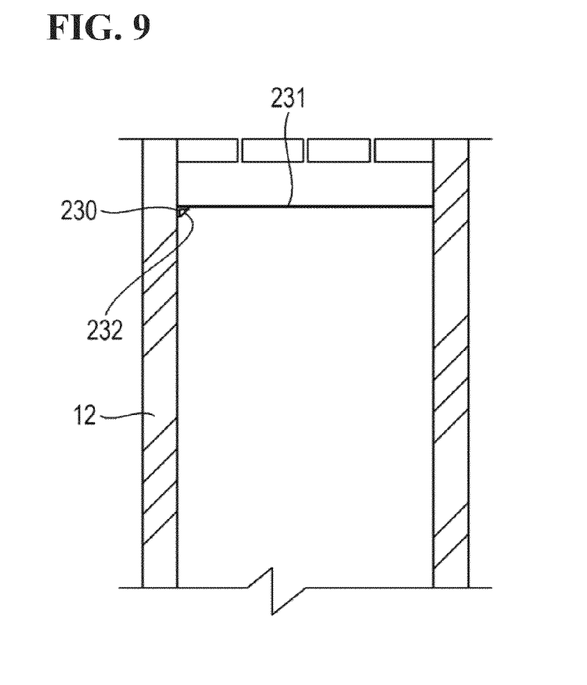
FIG. 9 is a vertical cross-sectional view illustrating the configuration of the bad odor removal system, installed in the sewerage manhole, according to the second embodiment of the present invention.

FIG. 8 is a horizontal cross-sectional view illustrating a configuration of the bad odor removal system, installed in a sewerage manhole 12, according to the second embodiment of the present invention, and FIG. 9 is a vertical cross-sectional view illustrating the configuration of the bad odor removal system, installed in the sewerage manhole 12.

As shown in FIGS. 8 and 9, the bad odor removal system 200 may further include a hinge 230 installed at the sewerage manhole 12 diverged from the sewage pipe 10, a bad odor dispersion-preventive plate 231 horizontally coupled with the hinge 230, and a spring 232 installed at the hinge 230 and elastically pushing up the bad odor dispersion-preventive plate 231.

When being formed as described above, usually, the bad odor dispersion-preventive plate 231 maintains level by elasticity of the spring 232, thereby preventing dispersion of a bad odor. When it rains or water flows from the outside, due to weight of the water, the spring 232 is elastically compressed and the bad odor dispersion-preventive plate 231 pivots downwardly around the hinge 230, thereby allowing the water to flow thereinto. After this, when the water does not flow therein any more, due to a restoring force of the spring 232, the bad odor dispersion-preventive plate 231 returns to an original position thereof and prevents the dispersion of the bad odor.

In this case, to provide airtightness of the bad odor dispersion-preventive plate 231, a sealing packing 233 may be disposed between the sewerage manhole 12 and the bad odor dispersion-preventive plate 231.

As described above, the bad odor dispersion-preventive plate 231 installed in the sewerage manhole 12 in the bad odor removal system 200 has been described above. The bad odor removal system 200 may include bad odor dispersion-preventive facility at an end of the sewage pipe 10, that is, a sewage outlet, in addition thereto, which will be descried below in detail with reference to the drawings.

Figure 10:
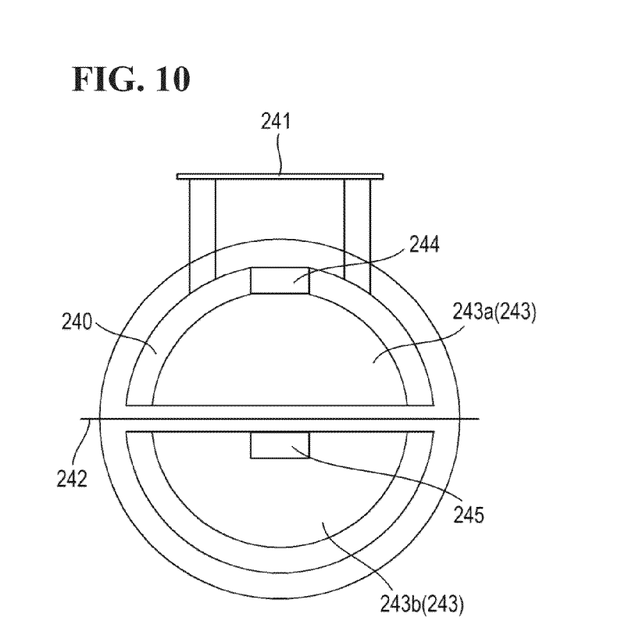
FIG. 10 is a vertical cross-sectional view illustrating a configuration of the bad odor removal system, installed at an end of the sewage pipe, according to the second embodiment of the present invention.
Figure 11:
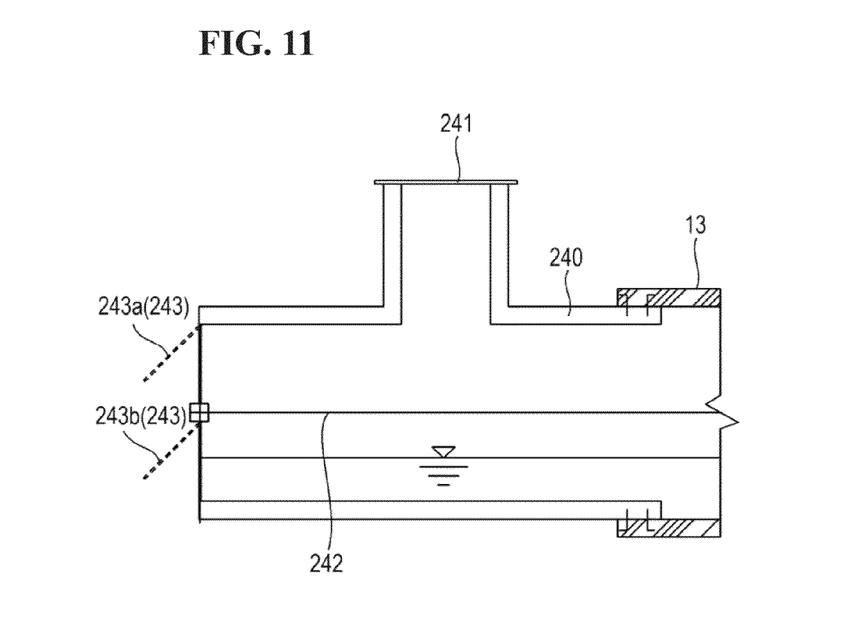
FIG. 11 is a side cross-sectional view illustrating the configuration of the bad odor removal system, installed at the end of the sewage pipe, according to the second embodiment of the present invention.

FIG. 10 is a vertical cross-sectional view illustrating a configuration of the bad odor removal system 200, installed at an end of the sewage pipe, and FIG. 11 is a side cross-sectional view illustrating the configuration of the bad odor removal system 200, installed at the end of the sewage pipe.

As shown in FIGS. 10 and 11, the bad odor removal system 200 may further include a bad odor dispersion-preventive pipe 240 installed at the end of the sewage pipe 10 and including a bad odor inlet port 241 connected to the outside and formed on a top of the bad odor dispersion-preventive pipe 240, a division strip 242 installed inside the bad odor dispersion-preventive pipe 240 and dividing the bad odor dispersion-preventive pipe 240 into an upper space and a lower space, and a bad odor dispersion-preventive plate 243 installed at ends of the upper space and the lower space to be pivotable outward.

In this case, the bad odor dispersion-preventive plate 243 may include a first bad dispersion-preventive plate 243a installed at a first supporter 244 of an inner top end of the bad odor dispersion-preventive plate 240 and a second bad dispersion-preventive plate 243b installed at a second supporter 245 of the division strip 242.

When being formed as described above, it is possible to prevent a residual bad odor of the sewage right before finally flowing into a septic tank or a sewage treatment plant via the sewage pipe 10.

In detail, the bad odor dispersion-preventive pipe 240 is inserted into and engaged with a sewage outlet, that is, an end 12 of the sewage pipe 10 and the first bad dispersion-preventive plate 243a and the second bad dispersion-preventive plate 243b are installed at the end of the bad odor dispersion-preventive pipe 240 by using hinges (not shown) to be usually closed and to be open only while discharging the sewage, thereby preventing the dispersion of the bad odor.

Accordingly, only the second bad odor dispersion-preventive plate 243b is open when discharging a small amount of the sewage, and the first bad odor dispersion-preventive plate 243a is also open when discharging a large amount of the sewage, thereby effectively preventing the bad odor. Also, since the division strip 242 prevents ascending of a bad odor of the lower part, a bad odor preventing effect may be maximized.

In this case, at the bad odor inlet port 241, the deodorizer 210 may be additionally installed to suck and remove a residual bad odor in the bad odor dispersion-preventive pipe 240.

Figure 12:
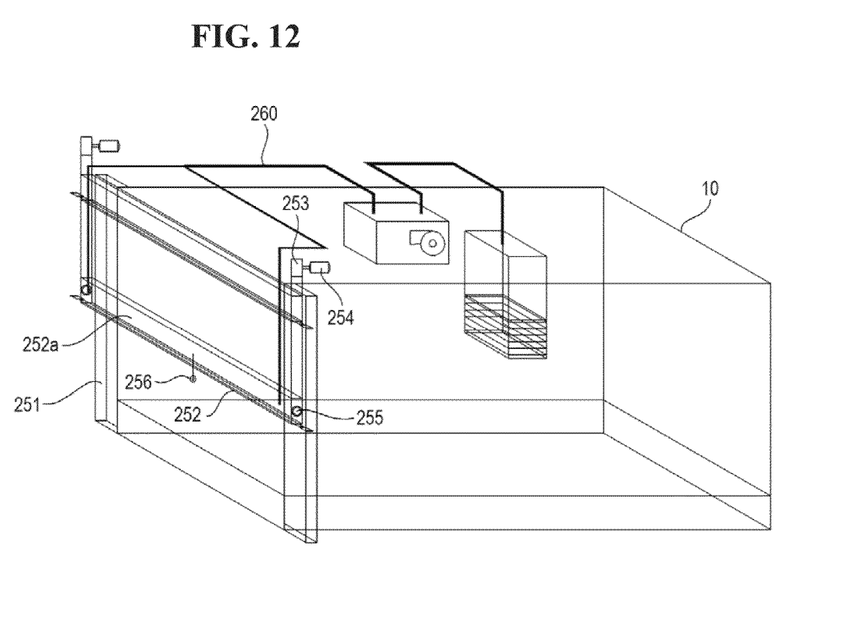
FIG. 12 is a view illustrating an air curtain of the bad odor removal system according to the second embodiment of the present invention.

On the other hand, different from the described above, an air curtain device 250 may be installed at the end of the sewage pipe 10, which will be described with reference to the drawing.

FIG. 12 is a view illustrating the air curtain device 250 of the bad odor removal system 200.

As shown in FIG. 12, the air curtain device 250 is a component to induce negative pressure inside the sewage pipe 10 and is installed at the end of the sewage pipe 10.

In detail, the air curtain device 250 includes a pair of guide rails 251 vertically installed at the end of the sewage pipe 10, an air curtain bar 252 assembled between the guide rails 251 to be slidable by using a pulley 254 and a fan belt (not shown) and connected to the deodorizer 210, and a lifting motor 253 coupled with the pulley 254 and vertically driving the air curtain bar 252.

In this case, in front of the air curtain bar 252, an outlet 252a is formed to allow purified air supplied via an exhausting duct 260 to be exhausted outward. In this case, a pivot axis 255 may be installed inside the air curtain bar 252 and gear-engaged with the guide rails 251 to vertically pivoting the air curtain bar 252 by using an angle-controlling motor (not shown), thereby controlling a direction of exhausting the purified air.

On the other hand, in the present embodiment, although the two air curtain bars 252 are installed at the top and bottom of the sewage pipe 10, the number of the installed air curtain bars 252 may be appropriately adjusted depending on the size of the sewage pipe 10.

A sensor 256 may be installed at the air curtain bar 252. The sensor 256 senses a temperature, humidity, an air flow, water level, and an air pollution degree of the atmosphere and may be installed at the guide rails 251 if necessary. In this case, various kinds of signals sensed by the sensor 256 are transmitted to the control device described in Embodiment 1 and gathered to be used to control vertical movement of the bad odor ventilating device, opening and closing the dampers, and turning on/off the deodorizers according to programs determined for each pattern, thereby uniformly maintain negative pressure induced inside the sewage pipe 10.

As described above, in the present embodiment, it is possible to perfectly block bad odors capable of being generated not only in a sewage pipe and sewerage manholes diverged from the sewage pipe but in a final outlet of sewage, thereby providing pleasant urban environment.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A bad odor removal system for a sewage pipe, the system comprising:
    deodorizers installed at an upper part of the sewage pipe with certain intervals; and
    a bad odor ventilating device connected to the deodorizers and installed inside the sewage pipe,
    wherein each of the deodorizers comprises a cooling device.

2. The system of claim 1, wherein the bad odor ventilating device comprises:
    a sucking unit connected to the deodorizer installed on an inner top end of the sewage pipe;
    an exhausting unit installed in the sucking unit; and
    a blast fan installed between the exhausting unit and the deodorizer.

3. The system of claim 2, wherein the sucking unit comprises:
    a support frame vertically installed on the inner top end of the sewage pipe;
    a sucking chamber installed inside the support frame and folded to be multistage;
    a fan belt connecting the sucking chamber; and
    a driving motor coupled with the fan belt.

4. The system of claim 3, wherein the exhausting unit comprises an exhausting chamber coupled with the fan belt to be foldable to be multistage inside the sucking chamber.

5. The system of claim 4, wherein at least one damper capable of being open and closed is installed outside one of the sucking chamber and the exhausting chamber.

6. The system of claim 5, further comprising a controller adjusting a direction of an air flow inside the sewage pipe by controlling operations of the respective components.

7. The system of claim 1, wherein a plurality of air flow blocking membranes is installed inside the sewage pipe to form a space for each of the deodorizers.

8. The system of claim 7, wherein each of the plurality of air blocking membranes comprises:
    supporters installed on the inner top end of the sewage pipe;
    a blocking membrane coupled with the supporters and divided with certain intervals;
    at least one wrinkle-preventive bar installed on the blocking membrane in a width direction; and centroid weights inserted into water-soluble or insoluble bags installed at a bottom of the blocking membrane.

9. The system of claim 1, further comprising:

a hinge installed at a sewerage manhole diverged from the sewage pipe and connected to the ground;

a bad odor dispersion-preventive plate coupled with the hinge; and a spring installed to the hinge and elastically pushing up the bad odor dispersion-preventive plate.

10. The system of claim 1, further comprising:

a bad odor dispersion-preventive pipe installed at an end of the sewage pipe;

a division strip installed inside the bad odor dispersion-preventive pipe and dividing the bad odor dispersion-preventive pipe into an upper space and a lower space; and bad odor dispersion-preventive plates installed outward at ends of the upper space and the lower space to be pivotable.

11. The system of claim 10, wherein a bad odor inlet port connected to a separate one of the deodorizers is formed on an upper part of the bad odor dispersion-preventive pipe.

12. The system of claim 2, wherein an air curtain device is installed at the end of the sewage pipe.

13. The system of claim 12, wherein the air curtain device comprises:

a pair of guide rails vertically installed at the end of the sewage pipe;

an air curtain bar coupled with the guide rails to be slidable and connected to the deodorizer; and a motor driving the air curtain bar.

14. The system of claim 13, wherein a sensor is installed on the air curtain bar.

* * * * *